United States Patent
Wysocki et al.

(10) Patent No.: US 8,528,553 B2
(45) Date of Patent: Sep. 10, 2013

(54) METHOD AND DEVICE FOR DETERMINING THE PEEP DURING THE RESPIRATION OF A PATIENT

(75) Inventors: Marc Wysocki, Chevreves (FR); Thomas Laubscher, Rhazuns (CH); Gion Durisch, Domat/Ems (CH); Josef Brunner, Chur (CH)

(73) Assignee: Hamilton Medical AG (CH)

( * ) Notice: Subject to any disclaimer, the term of this patent is extended or adjusted under 35 U.S.C. 154(b) by 1152 days.

(21) Appl. No.: 12/514,056

(22) PCT Filed: Nov. 14, 2007

(86) PCT No.: PCT/CH2007/000571
§ 371 (c)(1), (2), (4) Date: May 7, 2009

(87) PCT Pub. No.: WO2008/058417
PCT Pub. Date: May 22, 2008

(65) Prior Publication Data
US 2009/0301492 A1    Dec. 10, 2009

(30) Foreign Application Priority Data
Nov. 16, 2006 (CH) ........................ 1843/06

(51) Int. Cl.
*A61M 16/00* (2006.01)
(52) U.S. Cl.
USPC ............ 128/204.23; 128/204.21; 128/204.22; 128/204.18; 128/200.24
(58) Field of Classification Search
USPC ............... 128/204.18, 204.23, 204.21, 204.22
See application file for complete search history.

(56) References Cited

U.S. PATENT DOCUMENTS

| | | | | |
|---|---|---|---|---|
| 5,575,283 A | * | 11/1996 | Sjoestrand | 128/204.23 |
| 5,752,509 A | * | 5/1998 | Lachmann et al. | 128/204.23 |
| 5,937,854 A | * | 8/1999 | Stenzler | 128/204.23 |
| 6,192,885 B1 | * | 2/2001 | Jalde | 128/205.24 |
| 6,709,405 B2 | * | 3/2004 | Jonson | 600/538 |
| RE40,402 E | * | 6/2008 | Leonhardt et al. | 600/532 |
| 7,562,657 B2 | * | 7/2009 | Blanch et al. | 128/204.23 |
| 7,662,106 B2 | * | 2/2010 | Daniels et al. | 600/532 |
| 7,784,461 B2 | * | 8/2010 | Figueiredo et al. | 128/204.23 |
| 2003/0029452 A1 | * | 2/2003 | Suki et al. | 128/204.18 |
| 2003/0111078 A1 | | 6/2003 | Habashi | |
| 2004/0040560 A1 | * | 3/2004 | Euliano et al. | 128/204.23 |
| 2004/0055599 A1 | * | 3/2004 | Strom | 128/204.18 |

(Continued)

FOREIGN PATENT DOCUMENTS

| | | |
|---|---|---|
| DE | 10 2005 964 B3 | 7/2006 |
| EP | 0 671 180 | 9/1995 |
| WO | WO 03/037413 | 5/2003 |

*Primary Examiner* — Annette Dixon
(74) *Attorney, Agent, or Firm* — Morriss O'Bryant Compagni, PC (57) ABSTRACT

The invention relates to a device for the automated determination of the PEEP of a patient. Said device comprises sensors and a suitable electronic system for determining a pressure-volume characteristic curve during a P/V maneuver. The electronic system is designed in such a way as to generate, specifically in terms of breathing pressure, the difference between "lung volume during exhalation (Vdef)" and "lung volume during inhalation (Vinf)", and to determine the maximum value of said difference. The breathing pressure is then determined, for which the volume difference has a value defined in relation to the maximum value of the volume difference. The device calculates a PEEP value on the basis of said determined breathing pressure value.

25 Claims, 4 Drawing Sheets

(56) References Cited

U.S. PATENT DOCUMENTS

| | | |
|---|---|---|
| 2004/0073130 A1 | 4/2004 | Boehm et al. |
| 2005/0016534 A1* | 1/2005 | Ost .......................... 128/204.18 |
| 2005/0109340 A1* | 5/2005 | Tehrani .................... 128/204.21 |
| 2005/0211246 A1* | 9/2005 | Beck et al. ............... 128/204.23 |
| 2005/0284476 A1* | 12/2005 | Blanch et al. ............ 128/204.21 |
| 2006/0037616 A1* | 2/2006 | Seeger et al. ............ 128/204.23 |
| 2006/0162727 A1* | 7/2006 | Biondi et al. ............ 128/204.21 |
| 2006/0211950 A1* | 9/2006 | Brunner et al. .............. 600/538 |
| 2007/0062528 A1* | 3/2007 | Heinonen et al. ........ 128/204.21 |
| 2007/0062532 A1* | 3/2007 | Choncholas ............. 128/204.23 |
| 2007/0101992 A1* | 5/2007 | Soliman et al. .......... 128/204.21 |

* cited by examiner

METHOD AND DEVICE FOR DETERMINING THE PEEP DURING THE RESPIRATION OF A PATIENT

CROSS-REFERENCE TO RELATED APPLICATIONS

This application claims priority to PCT/CH2007/000571 filed on Nov. 14, 2007, and CH 1843/06 filed on Nov. 16, 2006, the entirety of each of which are incorporated by this reference.

BACKGROUND OF THE INVENTION

State of the Art

PEEP (positive end-expiratory pressure) refers to a positive pressure produced artificially in the lungs during ventilation, which is present after completion of exhalation (expiration). This pressure increases the mean pressure in the airways and the functional residual capacity. A PEEP can contribute to preventing collapse of the pulmonary alveoli. In many cases, oxygen saturation of the blood can be improved by means of a PEEP. For these reasons, at least a moderate PEEP is often used during machine ventilation.

However, ventilation with a PEEP can also have disadvantages. By increasing the pressure in the chest space, PEEP reduces the return flow of venous blood to the heart, and the cardiac output can drop as a result. Vice versa, a backup into the upper and lower vena cava occurs, with corresponding pressure increases in organs ahead of that. As a result, damage to and function restrictions of the brain, liver, kidneys and other organs can occur, depending on the level of the PEEP.

Modern ventilation devices offer detailed adjustment and measurement possibilities for PEEP ventilation. If the pressure is adjusted appropriately, the disadvantages of the positive pressure in the exhalation phase (risk of barotrauma at an overly high PEEP level, risk of damage to healthy lung areas, elevated right-ventricular afterload, increase in intracranial pressure) are offset by the advantages (increase in functional residual capacity, resulting in increase in gas exchange surface, ventilation/perfusion ratio, reduced intrapulmonary shunts, increased oxygenation, avoidance of atelectasis, improvement in compliance, reduction of a lung edema).

It is the task of the invention to create a device with which an appropriate PEEP can be automatically determined.

SUMMARY OF THE INVENTION

A device that accomplishes this task is provided by a device for automatically determining a PEEP adjusted to a patient, comprising sensors and suitable electronics for being able to determine a pressure/volume curve during a P/V maneuver. The electronics are designed to form a difference curve of the volumes during deflation and insufflation (Vdef−Vinf) to search for a maximum of this difference curve, to determine a value of the ventilation pressure at a volume of the difference curve defined in relation to the maximum and to determine a value for PEEP on the basis of this determined value of the ventilation pressure.

The device works according to the method for automatic determination of a PEEP adjusted to a patient, in which a pressure/volume curve is determined during implementation of a P/V maneuver, a maximum of the volume difference (Vdef−Vinf)max is sought for the pressure/volume curve determined in this manner, the value of the ventilation pressure is determined at a location of the difference curve that is defined in relation to the maximum (Vdef−Vinf)max, and the determined value of the ventilation pressure is used as a starting value for a determination of the PEEP.

Thus, the device according to the invention, for automatically determining a PEEP adjusted to a patient, comprises sensors and suitable electronics. Using these sensors, and the electronics that process the sensor measurement values, a pressure/volume curve can be determined during a P/V maneuver, in other words when a ventilation pressure is being increased and then reduced again—or when a high pressure level is reduced and then increased again. Such a pressure/volume curve can be determined using any suitable, known method, and using known devices. In this regard, reference is made to the state of the art as described in WO 03/037413 and also in DE 10 2005 000 964 B3, the entirety of each of which is incorporated by this reference.

It is practical, in this connection, if the volume that flows into the lungs of the patient, assigned to a ventilation pressure, in each instance, is added up, and the outflowing volume is subtracted. The difference approximately indicates the volume that was recruited by the ventilation pressure. The electronics are designed to form the difference of the lung volumes in a manner specific to the ventilation pressure. The lung volume during inhalation ("insufflation": Vinf) is subtracted from the lung volume during exhalation ("deflation": Vdef), in each instance, in a manner specific to the ventilation pressure. The electronics are furthermore designed to determine a difference maximum, and to determine a value of the ventilation pressure that prevails at a location of the difference curve that is defined in relation to the maximum. Consequently, a value for PEEP is calculated on the basis of the value of the ventilation pressure that is determined. A practical determination of this relevant location of the difference curve occurs in that an amount is subtracted from the maximum of the difference, and the locations that demonstrate this reduced difference are sought. Of the two such locations that generally exist, the one at which a lower ventilation pressure prevails than at the maximum is used.

A determination of the appropriate PEEP for the patient according to the invention, on the basis of the ventilation pressure at which the volume difference Vdef−Vinf is close to the maximum, has the advantage that this value of the ventilation pressure can be calculated very simply and automatically.

It is practical if the device is equipped with a display on which the value determined for the PEEP can be displayed. A device that is independent of the ventilation device is equipped with its own sensors. These can be inserted into the ventilation hoses of a ventilated patient, for example. Then, a pressure ramp of 0 to 40 mbar and back can be traveled with the ventilation device, for example. As this happens, the PEEP is automatically determined and displayed. A physician merely has to take this over and input it into the ventilation device. In place of a pressure ramp, a flow can also be controlled. For example, a constant flow can be generated. However, in this connection, the volume assigned to the pressure must also be recorded.

However, the device can also utilize the sensors of a ventilation device, in order to carry out the measurements required for calculating the PEEP.

Of course, a device tied in with a ventilation device or integrated into it also utilizes the sensors of the ventilation device and also the display of the ventilation device. In this case, the sensors can be integrated into the ventilation device or into the ventilation hose. The device can also be integrated into the ventilation device in such a manner that the value determined is automatically taken over by the ventilation device.

An advantageous device therefore has an electronic connection with a ventilation device or its control. This connection serves for transmission of the value determined for PEEP to the display and/or preferably to the control of the ventilation device.

The invention proceeds from the assumption that the value determined for the ventilation pressure at which the volume difference is greatest or almost greatest already corresponds very well to an appropriate PEEP for the patient. Therefore it can be taken over directly as a PEEP to be set. However, the possibility that at least in certain cases, a better setting is achieved if the measured pressure is still adjusted by means of calculations cannot be excluded. For this purpose, it can be provided that means are present in the device for selecting numerical values from a table or calculating them, in accordance with a disease profile and/or a body index of the patient. The electronics are then designed in such a manner that they process this value of the ventilation pressure with a numerical value selected or calculated using the aforementioned means, in order to determine the PEEP, for example exponentiate, multiply, or correct it by the selected or calculated numerical value.

It is advantageous if a PEEP or raised PEEP is not calculated in every case. For this reason, a limit value for the volume difference is established, and the electronics only determine a PEEP or a raised PEEP if the volume difference determined lies above this limit value. Volume differences that lie below this limit then indicate that the PEEP can be left at the previous value, or can actually be lowered.

It is practical if this limit value is dimensioned as a function of a body index of the patient. For example, height or an ideal weight can be used as a body index. Other factors that can be taken into consideration, or should be advantageous, are the disease profile of the patient and the age of the patient, i.e. whether the patient is a child or an adult.

It is practical if the device is provided with a time measurement device. This allows control of timed sequences. It is advantageous if the device is equipped in such a manner that it can control the increase and decrease in ventilation pressure and repeatedly trigger the determination of a new PEEP at certain time intervals. For this purpose, it can be integrated into the ventilation device, or possess its own means for generating a pressure increase and decrease.

The device can be combined with a ventilation device in such a manner that the ventilation device automatically takes over the value for PEEP that has been determined. This is possible even if the device is not part of the ventilation device. However, it is practical if such a device is integrated into ventilation devices with automatic adjustment of the ventilation to the needs of the patient.

Such a device functions according to the following method:

For automatic determination of a PEEP adjusted to a patient,

1. A pressure/volume curve is determined during implementation of a P/V maneuver. This is determined in that a ramp is moved up and down again with the ventilation pressure, for example, or in that a constant flow is generated, and the volume inhaled in this connection, assigned to the pressure, in each instance, is added up, and the exhaled volume, assigned to the pressure, in each instance, is subtracted again from the inhaled volume.

2. Then, the maximum of the volume difference $(Vdef-Vinf)max$ is determined for the pressure/volume curve determined in this manner.

3. Then, a value for the ventilation pressure is determined, which applies at a location of the difference curve that is defined in relation to the maximum.

4. And finally, this determined value of the ventilation pressure is used as a starting value for a determination of the PEEP.

In practice, it has been shown that the curve that represents the difference does not have a clear peak. It is therefore proposed that the appropriate PEEP should be determined in that a maximum is sought, proceeding from which a lower threshold value is established (selected or calculated as a function of age, height and/or disease profile of the ventilated person, e.g. 5, 10, 20, or 50 ml below the maximum), and finally, the lower of the two pressures that prevail at the locations at which the difference of the volumes has this lower threshold value is used as the basis for the PEEP. The lower value of the ventilation pressure is used as the starting point for the PEEP calculation, or as the PEEP.

It is also possible that there are several such locations. Then, the lower of the two values adjacent to the maximum can be used, or the lowest value can be used.

If the maximum of the difference is only determined after the entire P/V maneuver has been performed, both the maximum of the volume difference and the lowest value of the ventilation pressure on which the PEEP is to be based can be clearly determined.

However, this way of determining the relevant ventilation pressure also allows stopping the P/V maneuver when the ventilation pressure being sought has been reached. For this purpose, it is practical if the pressure is first built up in the lungs, and then reduced again. While it is being reduced, the difference can be calculated on an ongoing basis, in pressure-specific manner. As long as this difference is increasing, the new difference value counts as the maximum, in each instance. When the values drop, the highest value always counts as the maximum, specifically until a higher value is determined. If the volume then drops to a defined threshold value below the maximum, the then prevailing pressure is the starting value for the PEEP determination, or, directly, the pressure for the future PEEP setting.

Theoretically, it is possible that this value is too high, because later, at a lower ventilation pressure, an even higher maximum would have been measured. However, if the amount between the maximum and the lower threshold value is chosen to be sufficiently great, such a renewed increase in the volume difference can practically be excluded.

This determined value can be used directly as the PEEP, or also, if necessary, corrected by computer. This computed correction value is selected in accordance with a disease profile and/or a body index, for example. In this way, the patient and his/her needs can be individually taken into consideration. If a PEEP is calculated, the pressure difference within which the volume difference values lie within the aforementioned range can be included in the calculation.

It is advantageous if a limit value for the volume difference is established. If the determined volume difference lies above this limit value, a new PEEP is determined, or the current PEEP is increased in accordance with the result. If the determined volume difference lies below this limit value, the old PEEP is maintained, or a PEEP reduction is carried out. A PEEP reduction on the basis of this limit value not having been reached becomes unnecessary if the pressure was varied between zero and 40 mbar, for example, in the case of the pressure/volume curve being used. In this case, the PEEP can be set to a predetermined minimal value in the case of a maximal volume difference that lies below the limit value. However, if the limit value is exceeded, the newly found value of the ventilation pressure at the maximal volume difference applies as the PEEP, or as the basis for the PEEP determination.

It can be provided that the extent of an increase in the PEEP or a reduction of the PEEP is limited by maximal values. Then, greater PEEP changes are carried out in two or more steps that are spaced apart from one another in time. Such maximal values of the PEEP change remain at 5 mbar (possibly also +8 or +10 mbar), and at −2 or −3 mbar (possibly also −5 or −8 mbar), for example.

A PEEP determination can be triggered by the medical personnel, in each instance. The method can also be repeated automatically, at certain time intervals, in order to determine the current PEEP, in each instance.

In the case of automatic repetition of the method, there are two fundamentally different methods of procedure. In a first variant, the pressure ramp is started below the set PEEP, particularly at zero. This has the advantage that a PEEP that is lower than the present value can also be determined. The starting point can be selected to be zero or an intermediate value between zero and the set PEEP.

In a second variant, the pressure ramp is started at the previously set PEEP. This variant has the advantage that no collapse of pulmonary alveoli has to be accepted. It has the disadvantage that a lower PEEP cannot be determined. However, it can be provided that if a lower, second threshold value of the volume difference is not reached, a reduction in the PEEP is carried out.

If the method according to the invention is carried out in combination with mechanical ventilation, it is advantageous if the value determined for PEEP can be automatically set on the ventilation device. In this way, automatic regulation of the PEEP is achieved.

If the PEEP is increased, it is advantageous if a recruitment maneuver is performed, and afterwards, ventilation continues at the higher PEEP that has been determined. This is particularly practical if the ventilation pressure is lowered below the previous PEEP during the determination of the new PEEP value.

However, it can also be provided that a pressure ramp is traveled during exhalation, and that reduction of the ventilation pressure is stopped immediately as soon as the volume difference maximum was determined. Subsequently, ventilation continues at the newly determined PEEP.

DETAILED DESCRIPTION OF THE INVENTION

In the following, the invention will be described in detail using the diagrams shown in FIGS. 1 to 4. Figure one shows a P/V loop of a patient whose lungs are better ventilated using a PEEP. The lower ascending branch is formed in that the lungs are inflated, and the volume of the air blown in is plotted relative to the prevailing pressure. The upper descending branch is recorded while air escapes from the lungs and thus the pressure is reduced. In this connection, the air volume remaining in the lungs is plotted in relation to the prevailing pressure. The great difference between the ascending lower branch and the descending upper branch permits the conclusion that pulmonary alveoli have collapsed at a low ventilation pressure, but are open at a higher ventilation pressure.

For the physician, the question arises at what—lowest possible—PEEP the pulmonary alveoli that have been recruited will remain open. It was found that the appropriate PEEP can be read off on the loop, in a diagram according to FIG. 1. The appropriate PEEP is the pressure at which the greatest volume difference between Vdef and Vinf is measured.

Figure 1:
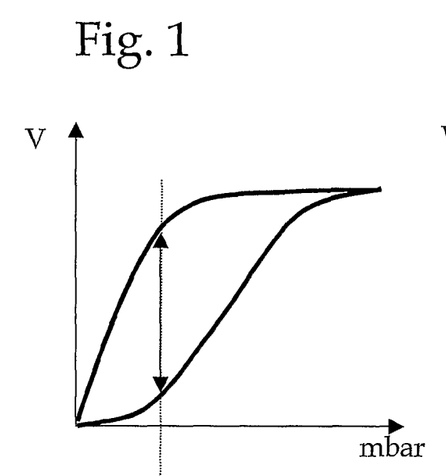
FIG. 1 schematically shows a first P/V loop with a great difference between Vdef and Vinf.

This location can be determined by means of forming the difference between Vdef and Vinf. In the case of a recruited volume (volume difference), the same location is defined, with only one peak, by the pressure at which the incline of the Vdef curve and of the Vinf curve is identical. Therefore, the tangents to the curves can also be sought, and the pressure at which the tangents to the ascending and the descending branch are parallel can be determined. However, it is simpler and safer to form the difference between the descending and the ascending branch. In the case of curves having two peaks, as well, a single value is generally obtained for the ventilation pressure at which the difference Vdef−Vinf reaches a maximum, using this difference formation.

Figure 2:
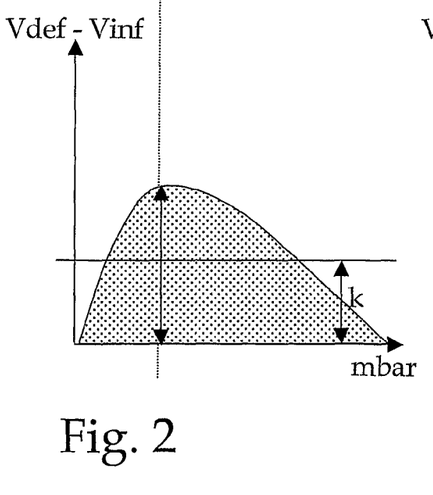
FIG. 2 schematically shows the difference formation between Vdef and Vinf for the first P/V loop.

This difference formation is furthermore very simple to calculate, and for this reason the peak of the curve according to FIG. 2—and with this, the desired value for the PEEP—can be determined very rapidly. The pressure at which the peak lies in FIG. 2 defines the pressure that—used as the PEEP—is suitable for keeping the pulmonary alveoli open.

In further tests, it can turn out that it is necessary to smooth out the measured curve, in order to be able to determine a clear peak. It can furthermore be found that it has a positive effect to add a pressure reserve of 2 mbar, for example, to this pressure that is in effect at the peak, in order to obtain an appropriate PEEP, or that an optimal PEEP can actually be reduced slightly as compared with the pressure that prevails at the peak.

Figure 3:
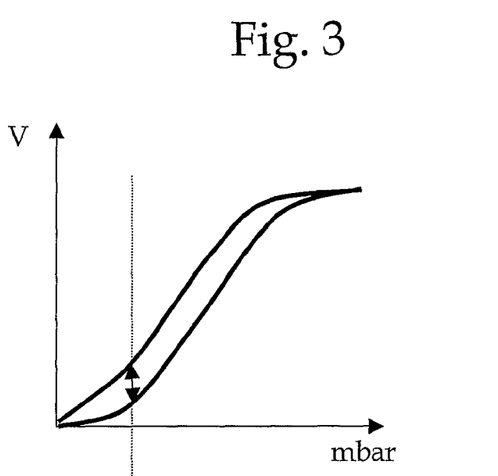
FIG. 3 schematically shows a second P/V loop with a small difference between Vdef and Vinf.
Figure 4:
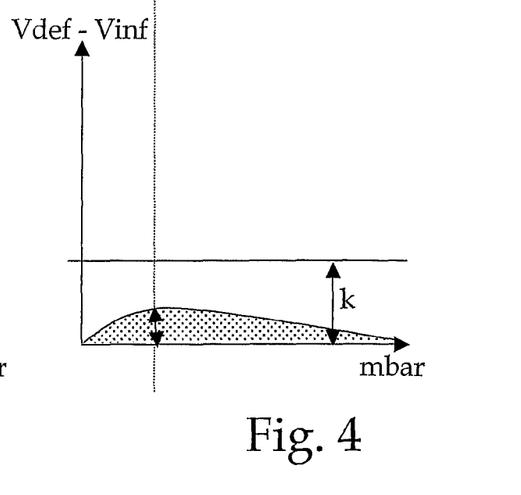
FIG. 4 schematically shows the difference formation between Vdef and Vinf for the second P/V loop.

FIGS. 3 and 4 show the same parameters as FIGS. 1 and 2. However, the measurements showed a relatively slight difference between Vdef and Vinf. Here, recruitment of additional alveoli is not possible. In the case of such a patient, it is therefore not necessary and not indicated to use an increased PEEP.

For this reason, and this is evident from FIGS. 2 and 4, there is a limit value for the Vdef−Vinf difference. This limit value has the amount k. The value of k, in each instance, can advantageously be established as a function of the patient (body index) and his/her disease profile.

If the determined volume difference has a maximal value that is less than k, no correction of the PEEP is carried out.

A PEEP is established only at a difference whose maximal value is greater than k.

This rule can also be applied to a PEEP correction in which a P/V loop is determined merely for the pressures above the set PEEP. Here, the limit value k can also be used to clarify whether or not a PEEP increase is practical. Experience has shown that this limit value k lies at 500 ml, on the average, in the case of an adult.

Figure 5:
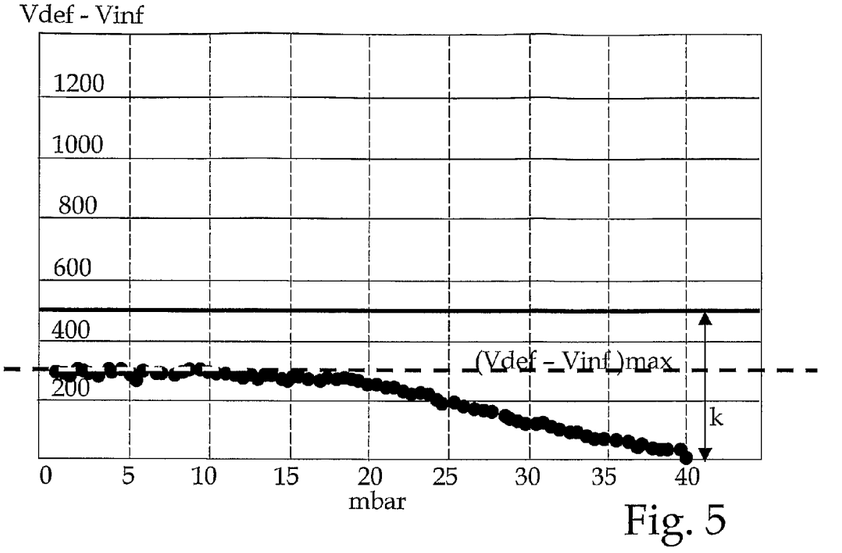
FIG. 5 shows a first difference formation of values measured on a person.
Figure 6:
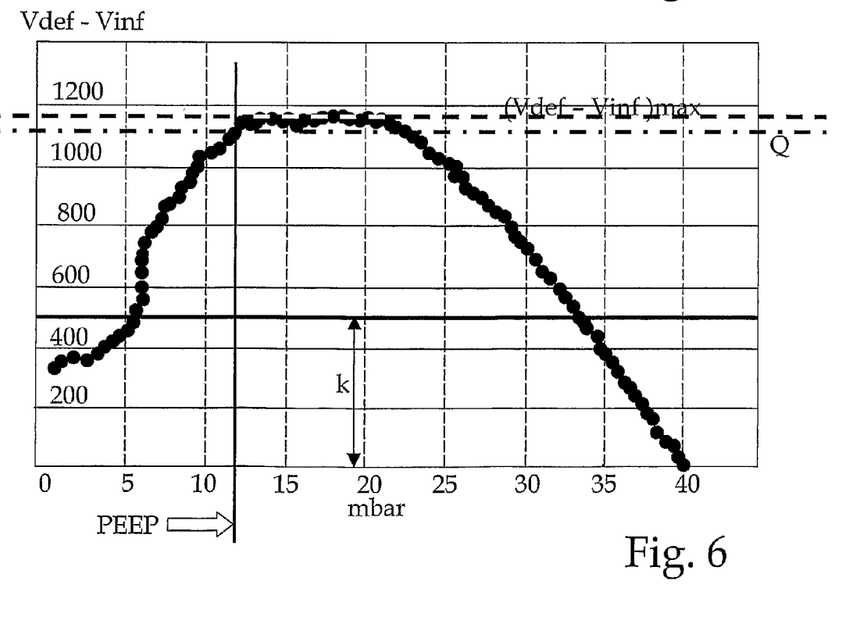
FIG. 6 shows a second difference formation of values measured on a different person.

FIGS. 5 and 6 show the volume difference diagrams of actual measurements. FIG. 5 shows the results for a lung in which an increase in the PEEP does not lead to recruitment of alveoli. FIG. 6 shows the results for a lung in which a PEEP of 12 mbar is necessary in order to keep most of the pulmonary alveoli open. From this FIG. 6, it is evident that smoothing of the curve can be helpful, in order to be able to determine a clear peak.

In FIG. 6, there is furthermore a lower threshold value (Q) at a defined distance from the peak of (Vdef−Vinf). The ventilation pressure on which the determination of the PEEP is based is only determined once the difference of the volumes reaches this threshold value. The PEEP can also be calculated on the basis of this ventilation pressure and of the ventilation pressure at the peak (e.g. lower pressure plus ⅓ of (upper pressure minus lower pressure)).

Figure 7:
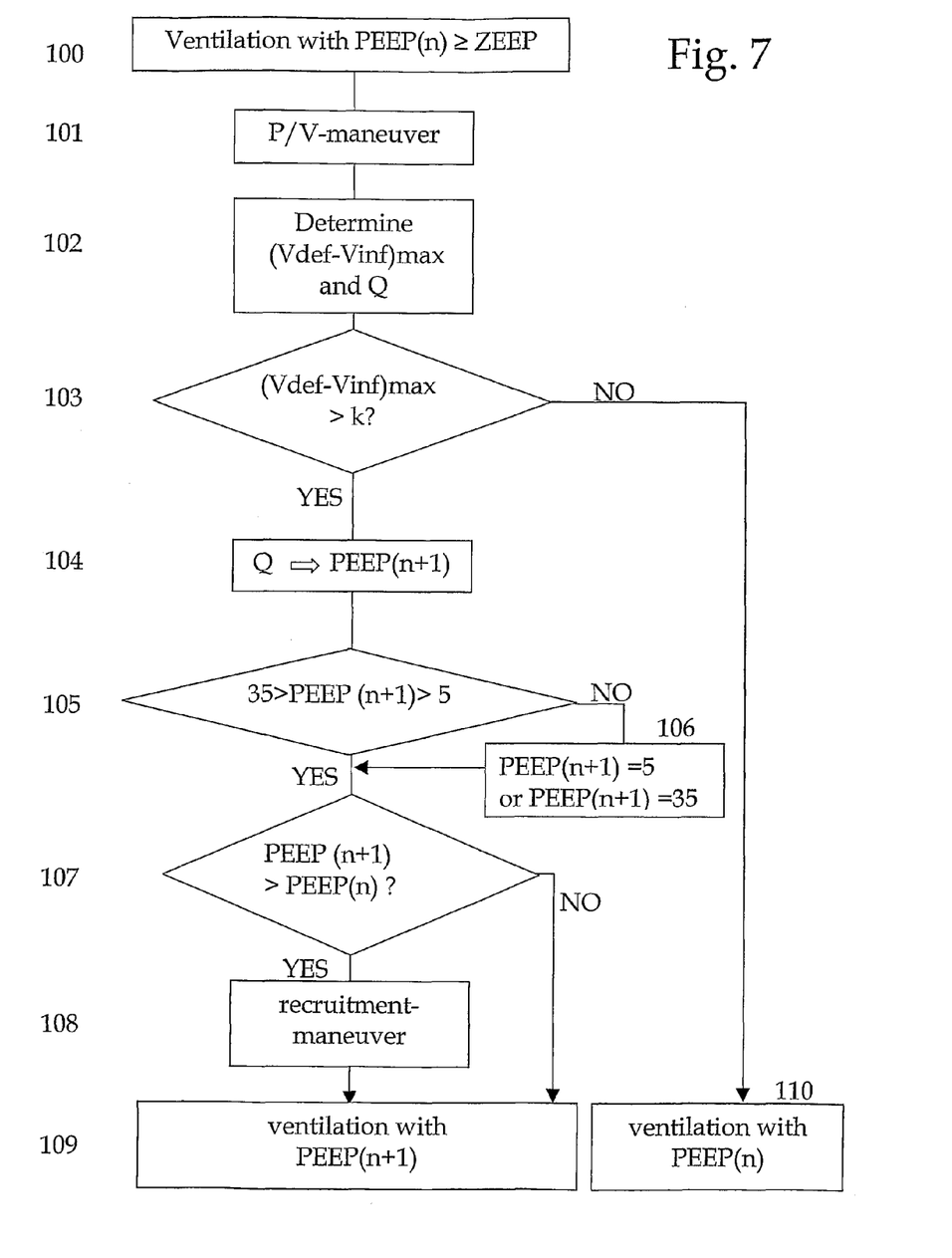
FIG. 7 shows a flow chart for the determination of the PEEP using the P/V loop.

The flow chart shown in FIG. 7 illustrates the sequence when determining the appropriate PEEP. The process starts with ventilation at any PEEP (Block 100). Before such a PEEP determination, the end-expiratory pressure can also be zero. Now, a P/V maneuver is carried out (Block 101). For this purpose, the pressure and the air volume in the lungs are increased and subsequently reduced again, according to one of many different methods that can be selected. During this process, the lung volume is recorded in relation to the pressure. The upper value of the pressure used in this connection lies at 40 mbar, for example. The lowest can be at 0, between zero and PEEP(n), or at the previous PEEP(n).

Subsequently or at the same time, the difference of the lung volume is calculated, and the maximal difference is determined (Block 102). With the difference maximum, the threshold value Q has also been determined. Once the maximal volume difference (or the threshold value Q) has been determined, a decision is made (Rhombus 103) as to whether or not this maximal volume difference (or the threshold value Q) exceeds the limit value k. If the determined volume difference is less than k, then ventilation continues with the previous end-expiratory pressure (Block 110), or the PEEP is reduced. The sequence variants for a reduction of the PEEP are not shown in FIG. 7.

A reduction of the PEEP is particularly indicated if the P/V loop was carried out only at pressures starting from the PEEP previously used. Criteria for PEEP reduction can be: value of the set PEEP, time since last PEEP increase, extent of the last PEEP increase, disease profile, age and body index of the patient, number of PEEP determinations without raising the PEEP.

An automatic PEEP reduction can be avoided if the PV maneuver is carried out at ventilation pressures beginning below the present PEEP (or actually at zero). The result obtained in this way is independent of the PEEP previously used.

It is therefore practical to carry the P/V maneuver out at certain time intervals (e.g. hourly, every three hours, every six hours, once to twice daily). In this connection, for example, a P/V maneuver can be carried out, proceeding from the previous PEEP, for as long as a PEEP needs to be raised, in each instance. If the appropriate PEEP determined in the manner according to the invention continues to remain the same after several (e.g. 3, 5, or 8) determinations, then afterwards, a P/V maneuver can be carried out proceeding from a lower pressure than the current PEEP(n) (for example, two thirds or half of PEEP(n)), when determining the PEEP. If, in this case, the new PEEP(n+1) lies lower than the previous PEEP(n), then, of course, this new PEEP(n+1) is used for further ventilation. In this manner, the frequency of collapse and renewed recruitment of the pulmonary alveoli can be reduced, and the value of the PEEP can nevertheless be corrected downward, if necessary.

Back to FIG. 7. Block 104 shows that the new PEEP(n+1) is determined on the basis of the location of the threshold value Q on the difference curve. In the simplest embodiment, this new PEEP can be the pressure at which the difference maximum or the pressure Q was determined. It can also deviate from this, but is definitely calculated proceeding from one of these pressures.

A next decision is that of determining whether the determined pressure lies above a first or below a second limit value, and accordingly, must be [word/words missing] to the limit value, in each instance (Rhombus 105). If the pressure determined for PEEP is 3 mbar, for example, then PEEP(n+1) is set to the lower limit value of 5 mbar, for example (Block 106). If it lies above 35 mbar, for example, then it is set to this value.

In practice, it will be shown whether or not such a limit value is even necessary. For example, only a lower limit value, on one side, might be necessary, because an upper limitation is already reached with the upper limitation of the pressure in the P/V loop.

If, however, it is found (Rhombus 107) that the new PEEP (n+1) is higher than the previous PEEP(n), then it is advantageous if a recruitment maneuver (Block 108) is carried out. This means that the pressure is increased, and that PEEP(n+1) is reached by this higher pressure. This is necessary in order to open all the pulmonary alveoli that remain open under this PEEP(n+1). Such recruitment can also be achieved by means of a P/V maneuver. No special recruitment maneuver is required, if the difference formation proceeds at the same time with the P/V maneuver, and the pressure at which the maximal volume difference (or at a certain distance from the maximum) prevails is used as the PEEP and does not drop below that.

Afterwards, ventilation can continue at the new PEEP(n+1) (Block 109).

Figure 8:
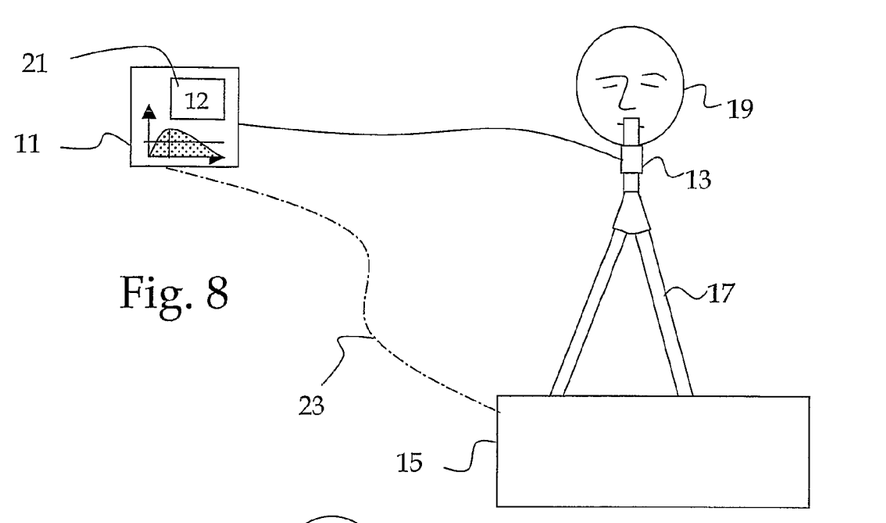
FIG. 8 shows a device for determining the PEEP in the manner according to the invention, which device is independent of a ventilation device.

The device 11 shown in FIG. 8 is equipped in such a manner that it can determine the PEEP according to the invention. It possesses a flow/pressure sensor 13, with which pressure and volume can be measured in known manner. This sensor is disposed on a ventilation hose 17, on the patient side, for example, or integrated into the device. The patient 19 is ventilated by means of the ventilation device 15, through this ventilation hose.

The device has a display 21 on which the value determined for PEEP is displayed. For the determination of the appropriate PEEP, the ventilation pressure is increased and lowered again, using the ventilation device 15. Pressure and volume are measured in the sensor 13, and the suitable PEEP is calculated from this, using the electronics.

An optional connection between the device according to the invention and the ventilation device is shown with the broken line 23. The value for PEEP can be input directly into the system of the ventilation device by way of this connection 23, and/or a P/V maneuver can be triggered.

Figure 9:
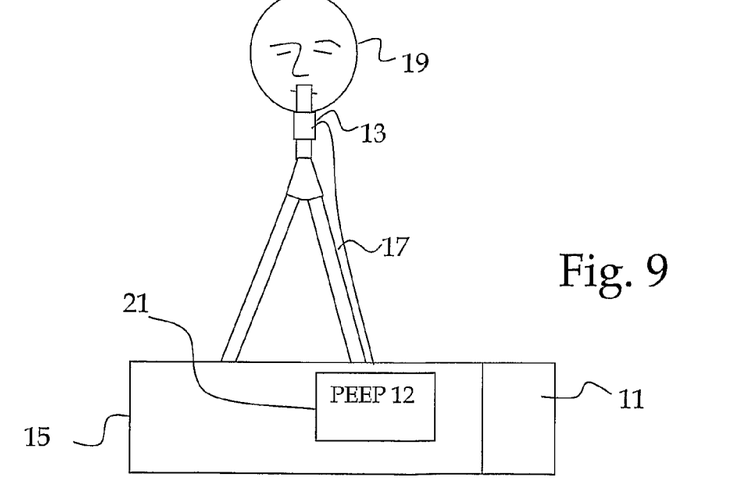
FIG. 9 shows a ventilation device having a device according to the invention integrated into it.

In FIG. 9, the device 11 according to the invention is integrated into the ventilation device 15. The pressure source of the ventilation device 15 and the pressure/flow sensor 13 of the ventilation device are used to create the P/V loop. The value for PEEP can be shown on the display 21, and/or can be automatically used for ventilation.

The invention claimed is:

1. A device for automatically determining a positive end-expiratory pressure adjusted to a patient, comprising:
sensors and electronics for determining a pressure/volume curve during a pressure-volume maneuver, said electronics configured to:
generate a difference curve of volumes during deflation and insufflation;
determine a maximum of the difference curve;
determine a ventilation pressure value at the maximum; and
determine a positive end-expiratory pressure value the ventilation pressure value.

2. The device according to claim 1, further comprising a display in communication with the electronics for displaying the values determined for positive end-expiratory pressure.

3. The device according to claim 1, further comprising an electronic connection between the electronics and a ventilation device configured for at least one of transmitting the value determined for positive end-expiratory pressure and triggering a pressure-volume maneuver.

4. The device according to claim 3, wherein the electronic connection is configured for controlling the ventilation device, in order to automatically use the value determined for the positive end-expiratory pressure as a basis for ventilation.

5. The device according to claim 1, wherein the determined value of the ventilation pressure is used as the positive end-expiratory pressure.

6. The device according to claim 1, wherein the electronics establish a lower threshold ventilation pressure value relative to the determined ventilation pressure value by selecting at least one numerical value corresponding to at least one of a disease profile of the patient and a body index of the patient from a table, or by calculating at least one numerical value based on at least one of the disease profile of the patient and the body index of the patient, the electronics configured to determine the positive end-expiratory pressure value from the lower threshold ventilation pressure value.

7. The device according to claim 1, wherein the electronics set a limit value for the volume difference, and the electronics only determine an increased positive end-expiratory pressure if the maximum of a volume difference lies above the limit value.

8. The device according to claim 7, wherein the limit value is a function of at least one of a body index of a patient and a disease profile of the patient.

9. The device according to claim 8, wherein the ventilation pressure on which the positive end-expiratory pressure is based is the lowest of the pressures that prevail at locations at which the difference curve has a volume value that lies a defined amount below the maximum.

10. The device according to claim 9, wherein the defined amount is established by the limit value, as a function of at least one of the body index of the patient and the disease profile of the patient.

11. The device according to claim 1, wherein the electronics comprise a time measurement device and configured to control at least one of the pressure ramp of the ventilation pressure and repeated triggering of a determination of a new positive end-expiratory pressure at certain time intervals.

12. The device according to claim 1, wherein the sensors and electronics are combined with a ventilation device, in such a manner that the ventilation device automatically takes over the determined positive end-expiratory pressure value.

13. The device of claim 1, wherein the sensors and electronics further comprise a ventilation device.

14. A method for automatic determination of a positive end-expiratory pressure adjusted to a patient, comprising:
determining a pressure/volume curve during implementation of a pressure-volume maneuver using at least one sensor and electronics for use in combination with a ventilation device by generating a difference curve of lung volumes of a patient during deflation and insufflation from a plurality of volumes measured by the at least one sensor and electronics during deflation and insufflation;
using the electronics to determine a maximum of the lung volume difference for the pressure/volume curve;
using the electronics to determine the value of the ventilation pressure at a location of the difference curve that is defined at the maximum of the volume difference; and
using the determined value of the ventilation pressure as a starting value for determining the positive end-expiratory pressure for a ventilation device.

15. The method according to claim 14, further comprising using the value of the ventilation pressure as the positive end-expiratory pressure.

16. The method according to claim 14, further comprising using the electronics to process the determined value with a numerical value, the numerical value selected or calculated in accordance with at least one of a disease profile and a body index.

17. The method according to claim 14, further comprising using the electronics to establish a limit value for the volume difference, and to determine a new positive end-expiratory pressure if the maximum of the volume difference lies above the limit value, and to either not determine a new positive end-expiratory pressure or perform a positive end-expiratory pressure reduction if the determined volume difference lies below the limit value.

18. The method according to claim 17, further comprising using a threshold ventilation pressure on which the positive end-expiratory pressure is based that is below the pressure prevailing at the maximum of the volume difference.

19. The method according to claim 18, further comprising determining the threshold pressure at the limit value for the volume difference, as a function of at least one of a body index of the patient and a function of the patient's disease profile.

20. The method according to claim 14, further comprising repeating the method at certain time intervals.

21. The method according to claim 14, further comprising starting the pressure-volume maneuver at a pressure below the starting value of the positive end-expiratory pressure.

22. The method according to claim 14, further comprising starting the pressure-volume maneuver at the starting value of the positive end-expiratory pressure.

23. The method according to claim 14, further comprising automatically setting the starting value of the positive end-expiratory pressure on the ventilation device.

24. The method according to claim 14, further comprising, after determining the positive end-expiratory pressure, performing a recruitment maneuver, and afterwards, performing ventilation by the ventilation device using the positive end-expiratory pressure that has been determined.

25. The method according to claim 14, further comprising calculating each volume difference of the plurality of volume differences while the pressure-volume maneuver is performed, and stopping the pressure-volume maneuver during deflation, as soon as the volume value defined in relation to the maximum of the volume difference has been determined, and subsequently, continuing ventilation with the ventilation device at the positive end-expiratory pressure that has been determined.

* * * * *